United States Patent [19]

Sokolovsky

[11] Patent Number: 4,537,059
[45] Date of Patent: Aug. 27, 1985

[54] AUTOMATIC BRUSHING MACHINE

[75] Inventor: Paul J. Sokolovsky, Sunnyvale, Calif.

[73] Assignee: Advanced Micro Devices, Inc., Sunnyvale, Calif.

[21] Appl. No.: 522,910

[22] Filed: Aug. 12, 1983

[51] Int. Cl.³ .............................................. G01N 3/56
[52] U.S. Cl. ......................................................... 73/7
[58] Field of Search ........................................ 73/7, 8

[56] References Cited

U.S. PATENT DOCUMENTS

| | | | |
|---|---|---|---|
| 2,966,790 | 1/1961 | Walker | 73/7 |
| 3,323,349 | 6/1967 | Savage et al. | 73/7 |
| 3,929,001 | 12/1975 | Lee et al. | 73/7 |
| 3,961,521 | 6/1976 | Bailey et al. | 73/7 |
| 4,196,611 | 4/1980 | Suga | 73/7 |

FOREIGN PATENT DOCUMENTS

| | | | |
|---|---|---|---|
| 1030586 | 5/1958 | Fed. Rep. of Germany | 73/7 |
| 2262956 | 7/1974 | Fed. Rep. of Germany | 73/7 |
| 498000 | 9/1954 | Italy | 73/7 |
| 485862 | 1/1976 | U.S.S.R. | 73/7 |
| 502293 | 4/1976 | U.S.S.R. | 73/7 |
| 693146 | 11/1979 | U.S.S.R. | 73/7 |

OTHER PUBLICATIONS

"Wear Testing Machine", *Industrial Laboratory*, vol. 40, No. 7, pp. 1082–1083, L. E. Semenov, 1–1975.

Primary Examiner—Stewart J. Levy
Assistant Examiner—Tom Noland
Attorney, Agent, or Firm—Patrick T. King; James M. Heslin

[57] ABSTRACT

An apparatus for quality control testing of semiconductor packages comprises a support platform for holding a device in a fixed location and a reciprocatable brush which is mounted to contact the device with a constant force. The reciprocating mechanism basically moves the brush horizontally across a test package but is linked with a cam system for elevating the brush out of contact with the test package during one of the strokes and lowering the brush back into contact with the test package during the other stroke. Highly accurate and repeatable abrasion tests can thus be performed.

7 Claims, 3 Drawing Figures

AUTOMATIC BRUSHING MACHINE

BACKGROUND OF THE INVENTION

1. Field of the Invention

The present invention relates generally to the field of quality control testing, and more particularly to an apparatus and method for testing semiconductor device packages for abrasion resistance.

Semiconductor devices are typically encapsulated in a plastic or ceramic material in order to protect the device from damage. The resulting structures, referred to hereinafter as semiconductor device packages, have conductive leads brought out through the protective material and are typically mounted on printed circuit boards in building larger electronic systems.

Semiconductor device packages are usually marked to identify the particular device which has been encapsulated. Information such as the manufacturer, the type of device, the identity of the electrical leads, and the like, will be imprinted on the package in a permanent manner. It is important that the printed information remain on the package, and steps are taken to assure that the markings will not be lost even in hostile environments.

To assure the adequacy of the package markings, certain quality control tests have been devised. In particular, methods 5005 and 2015 of Military Standard 883 (MIL-STD-883) call for immersing the semiconductor devices in various solvents and thereafter brushing the outer surface of the package and examining the package for damage. If the package is damaged in any way, particularly if the markings are missing in whole or in part, faded, smeared, blurred, or dislodged, the packages has failed the quality control test.

In any quality testing, such as that specified by MIL-STD-883, it is critically important that the testing be carried out in a highly repeatable manner. Each step of the testing must be performed pursuant to specific parameters, and deviations from these parameters individual tests must be avoided. Any step which cannot be precisely controlled, such as steps which require subjective human judgement, will introduce error and non-repeatability into the test.

As heretofore carried out, the brushing step performed under MIL-STD-883 has been accomplished manually. Such manual brushing can lead to widely varying results. A package which sustains no damage when lightly brushed, might well be harmed by more vigorous treatment. Conversely, few packages would be able to withstand the onslaught of a determined individual wielding a brush.

For these reasons, it would be desirable to provide an apparatus and method for uniformly testing semiconductor device packages. In particular, it would be desirable to provide an automated system which eliminates human judgement from the brushing step of the above-described testing procedure and which produces repeatable results.

2. Description of the Prior Art

The patent literature reveals a number of devices intended to test the effect of mechanical abrasion on various articles. See, e.g., U.S. Pat. No. 4,196,611 to Suga; U.S. Pat. No. 2,966,790 to Walker; U.S. Pat. No. 2,950,617 to Campbell; U.S. Pat. No. 2,929,240 to Williams, U.S. Pat. No. 2,734,375 to Galbraith et al.; U.S. Pat. No. 2,590,839 to Clapham; and U.S. Pat. No. 2,519,556 to Fish. None of these patents disclose the use of a reciprocating brush under constant load for abrasion testing.

A number of devices employing rotary brushes for cleaning glass, bottles and the like have been proposed. See, e.g., U.S. Pat. No. 2,636,199 to Stanton, et al.; U.S. Pat. No. 1,921,680 to Kopnicky; U.S. Pat. No. 957,301 to Buchheit; U.S. Pat. No. 876,706 to Failing; U.S. Pat. No. 787,858 to Schafer; U.S. Pat. No. 583,283 to Donally; U.S. Pat. No. 518,275 to Rantz; and U.S. Pat. No. 490,682 to Roemer. None of these patents disclose devices having reciprocating brushes under constant load suitable for abrasion testing.

SUMMARY OF THE INVENTION

A method and apparatus are provided for abrasion testing of individual test pieces, typically semiconductor device packages. The apparatus supports the test piece in a fixed position and draws a brush over the test piece in a repeatable cycle. The brush is mounted so that it exerts a predetermined force on the test piece during each stroke, thus assuring the repeatability of the test procedure.

In the preferred embodiment, the brush is mounted in a brush holder having a preselected weight. The brush holder, in turn, is pivotally secured to a horizontal rod, and a mechanism is provided for reciprocating the rod in a horizontal direction so that the brush travels over the test piece. A cam surface in combination with a wedge-shaped support beneath the brush holder is provided to raise the brush in an elliptical arc over the test piece during the forward stroke of the reciprocation cycle. During the backstroke cycle, the brush is gently lowered into contact with the test piece. The brush contacts the test piece with a fixed and repeatable force.

DESCRIPTION OF THE PREFERRED EMBODIMENTS

Figure 1:
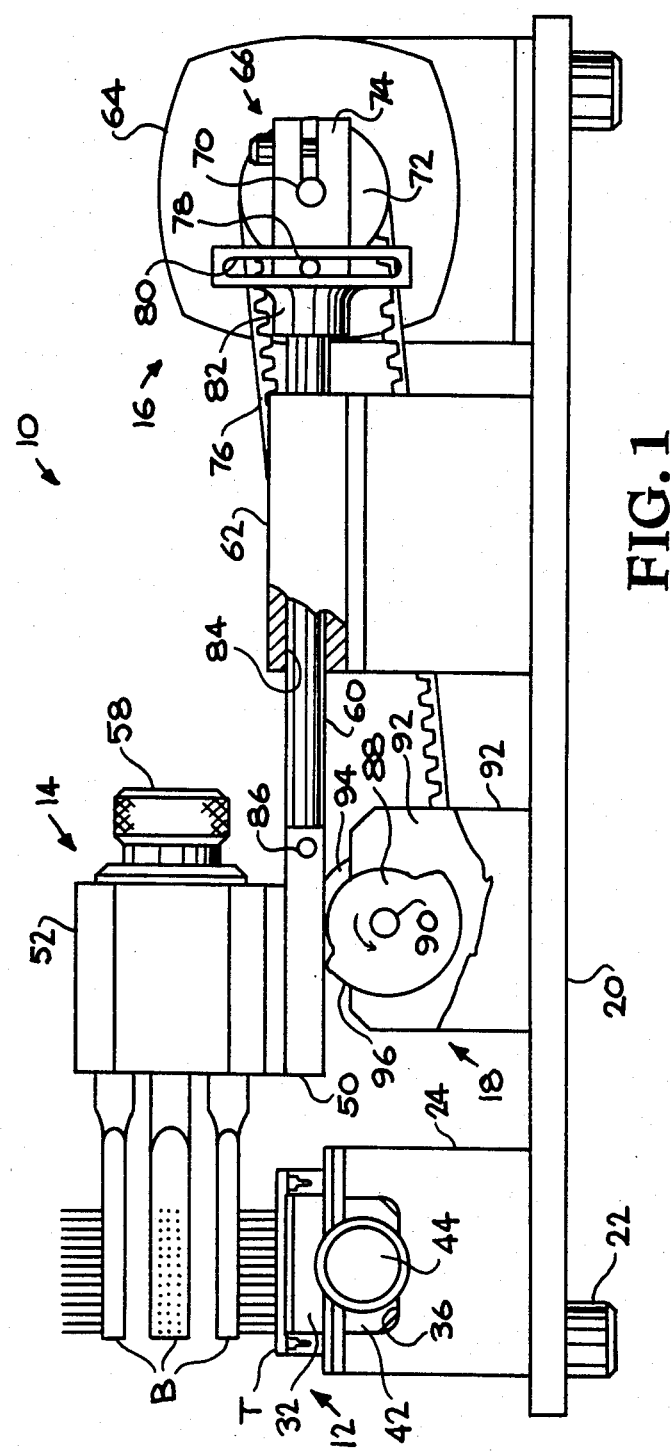
FIG. 1 is a front elevational view of the apparatus of the present invention with portions broken away.
Figure 2:
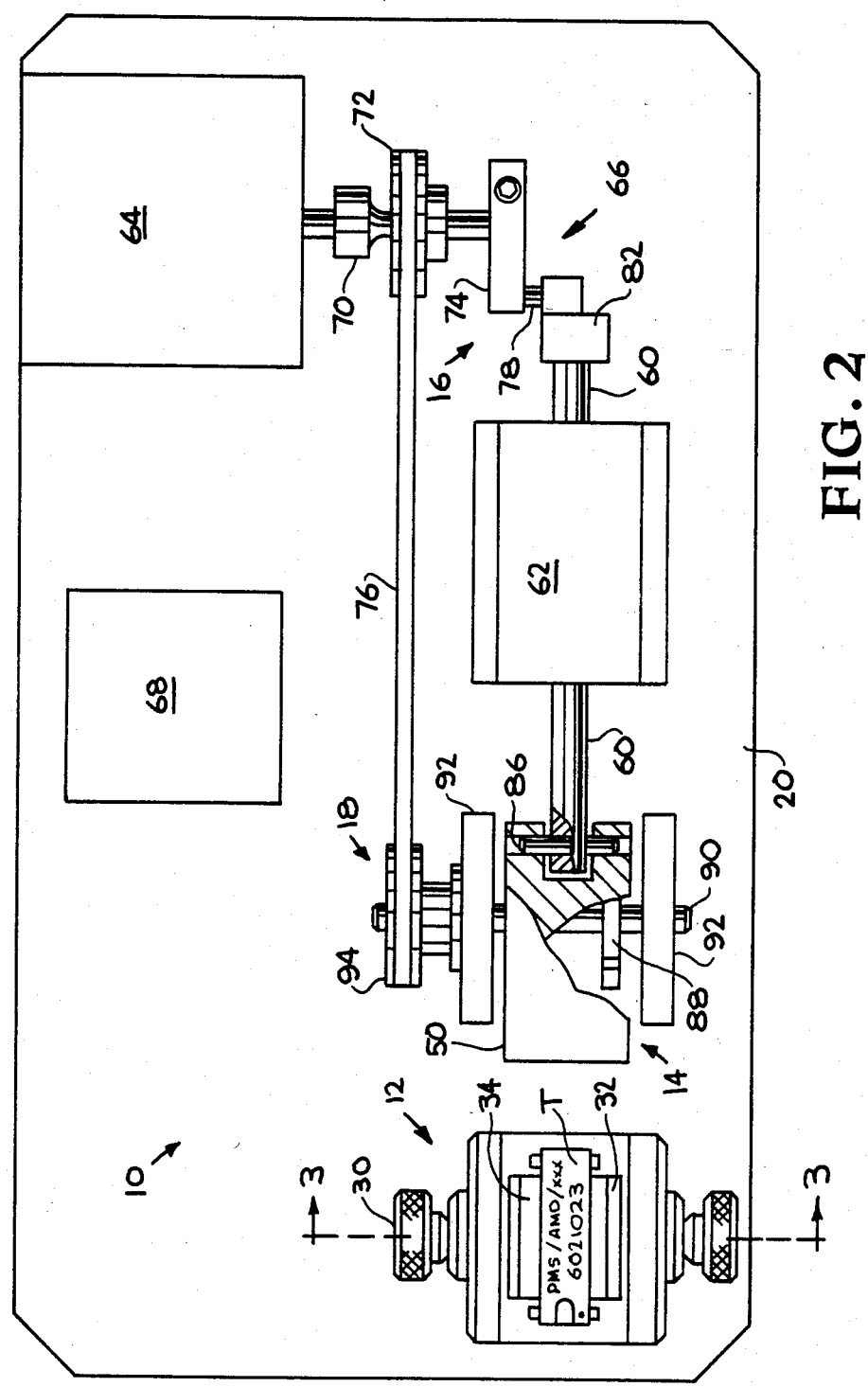
FIG. 2 is a top plan view of the apparatus of the present invention with portions broken away.
Figure 3:
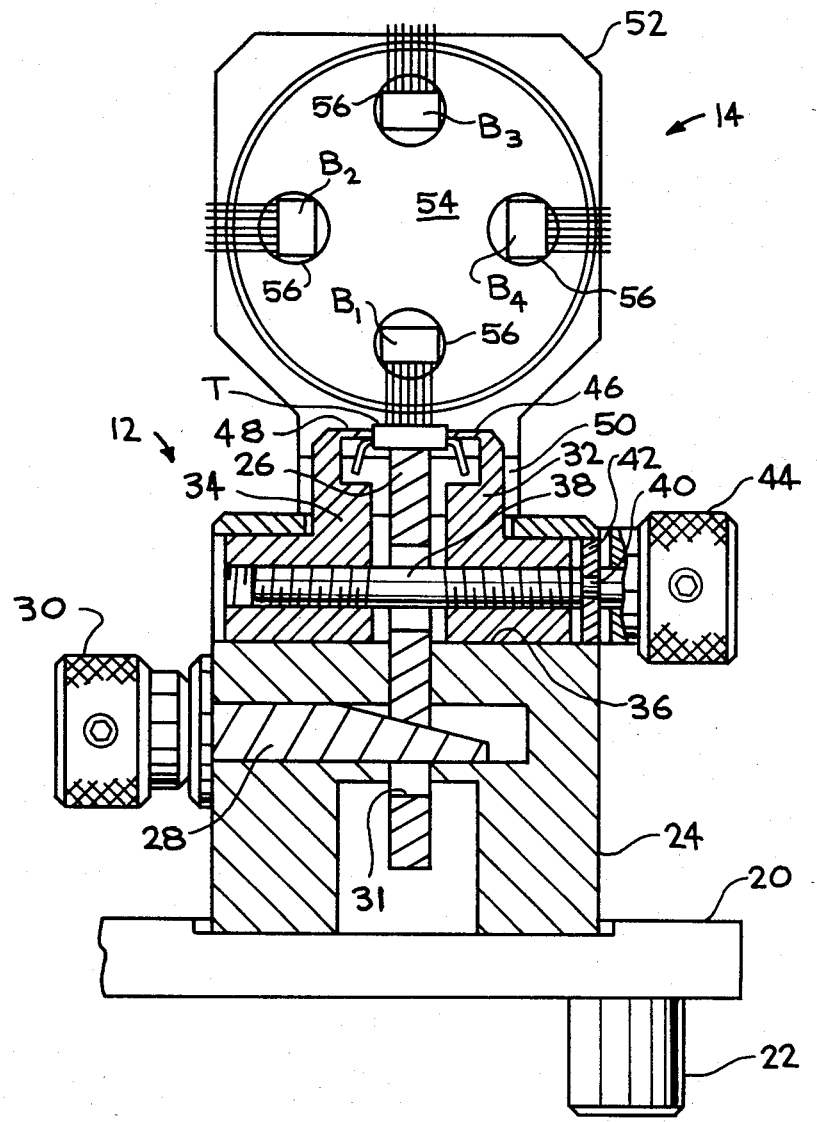
FIG. 3 is a sectional view taken along line 3—3 in FIG. 2.

Referring to FIGS. 1-3, an automatic brushing apparatus 10 constructed according to the principles of the present invention will be described. The apparatus 10 includes a support platform 12 for holding a test piece T in a fixed position, a brush holder 14 having a predetermined weight (typically one pound), a drive assembly 16 for reciprocating the brush holder 14 along a straight horizontal path, and a cam assembly 18 for raising and lowering the brush holder 14 as it is reciprocated. All the assemblies 12, 14, 16 and 18 are mounted on a base 20 which includes feet 22 on its lower surface for mounting on a table top or other horizontal surface. Each of the assemblies will now be described in more detail.

The support platform 12 is designed to hold work pieces T having different dimensions. As illustrated in FIGS. 1-3, the work piece T is a dual in-line package (DIP), a type of semiconductor package commonly employed in the semiconductor industry. The package T is supported on a vertical post 26 (FIG. 3) which in turn is received on a sliding wedge 28. Both the vertical post 26 and sliding wedge 28 are mounted in a support block 24. The wedge 28 may be translated to the left or right (in reference to FIG. 3) within block 24 by knob 30. Knob 30 is connected to wedge 28 by a conventional threaded connector (not shown). As the wedge 28 is moved toward the right, a cam partially defining an aperture 31 in post 26 travels up the inclined surface of the wedge, causing the post to rise. Conversely, as sliding wedge 28 is moved toward the left, the vertical post 26 is lowered. In this way, the elevation of the work piece T can be precisely adjusted. Such precise adjustment is important, as will be described hereinafter, in order to maintain the proper contact between brushes B (mounted on brush holder 14) and the test piece T.

The test piece T is held in place on vertical post 26 by jaws 32 and 34. Jaws 32 and 34 are mounted in a channel 36 (FIG. 3) formed across the upper end of support block 24. The jaws are mounted on a threaded shaft 38. The threads running through jaw 32 are oriented in the opposite direction as the threads running through jaw 34. In this way, rotation of the shaft 38 in a first direction causes the jaws to move toward one another, while rotation in the opposite direction causes the jaws to move away from each other. The shaft 38 includes an annular depression 40 which is received in plate 42 secured to block 24. Thus, rotation of shaft 38 by knob 44 causes jaws 32 and 34 to move symmetrically relative to post 26. Flanges 46 and 48 on jaws 32 and 34, respectively, are thus able to clamp onto the test piece T, as best illustrated in FIG. 3. As thus described, means are provided for removably supporting test pieces T of varying dimensions at a fixed location in the automatic brushing apparatus 10.

The brush holding assembly 14 comprises a wedge plate 50 and a cylinder housing 52 mounted on the upper surface of plate 50. Cylinder housing 52 rotatably receives a brush-holding cylinder 54 (FIG. 3) having receptacles 56 formed in its forward (i.e., to the left in FIG. 1) face. Receptacles 56 are sized to receive standard industrial brushes of a type suitable for performing the abrasion test of the present invention. As will be explained hereinafter, different brushes B will be required for different tests. A particular brush may be selected for each test by rotating knob 58 which is connected directly to the cylinder 54.

The drive assembly 16 includes a drive rod 60, rod support housing 62, drive motor 64 and linkage assembly 66 which converts the rotary motion of motor 64 into a linear reciprocation for drive rod 60. Tyically, a conventional motor controller 68, such as a SCR motor controller, will be provided to vary the speed of the motor 64.

The linkage assembly comprises a coupling 70 mounted on the drive shaft motor 64. Mounted on the coupling 70 are a sprocket 72 and a drive arm 74. The sprocket 72 carries a timing belt 76 which drives the cam assembly 18 in unison with the drive rod 60, as will be described hereinafter.

Drive arm 74 carries a pin 78 which is spaced radially outward from the center line of coupling 70. Pin 78 is received in slot 80 of follower 82 which is mounted on the rear (i.e., to the right in FIG. 1) and of drive rod 60. Drive rod 60 is mounted in an elongate bearing 84 in rod support housing 62. Rod 60 is thus able to move only along a straight line in the horizontal plane. Thus, the circular motion of pin 78 in slot 80 causes the horizontal reciprocation of drive rod 60.

Wedge plate 50 of brush holding assembly 14 is pivotally attached to the forward end of drive rod 60 on pin 86. Thus, in the absence of cam assembly 18, brush holding assembly 14 is free to rotate about the pivot point defined by pin 86. Rotation of brush holding assembly 14 will also be prevented by contact between the lowermost brush $B_1$ with the test piece T, as will be described hereinafter. In this way, the test piece T supports a constant load whose magnitude depends solely on the weight of the brush holding assembly 14 and the distance between pivot point 86 and the test piece T.

The cam assembly 18 is provided to elevate the brush holding assembly 14 during its forward stroke so that the brush $B_1$ contacts the test piece T only during the backward stroke. Cam assembly 18 comprises a pair of rotary cams 88 (only one being shown in FIGS. 1 and 2) rotatably mounted on shaft 90 supported on vertical plates 92. A sprocket 94 is secured to the shaft 90 and driven by timing belt 76 mounted at its other end on sprocket 72. By properly selecting the relative diameters of both sprockets 72 and 94 as well as the cam 88, the peripheral speed of the cam surface will match the linear speed of lower platform 50 when they come into contact.

As illustrated in FIG. 1, the raised portions 96 of cams 88 are just contacting wedge platform 50, and drive rod 60 is in its forwardmost position. Drive arm 74 is being driven in the counterclockwise direction, and the cam 88 (which also rotates counterclockwise) remains out of contact with the wedge plate 50 during the backstroke of the brush $B_1$. Thus, the brush $B_1$ is able to stroke the test piece T during the backstroke. After drive arm 74 has rotated 180°, drive rod 60 is in its fully rearward position and the raised portions 96 of the cams 88 contact wedge plate 50 and lift brush $B_1$. The direction of travel of rod 60 reverses, and the brush $B_1$ is carried forward over (out of contact with) the test piece T. Conveniently, the wedge plate 50 is tapered in the direction of pivot pin 86 so that the brush is gently lowered during its forward stroke, just contacting the test piece as the brush reaches its forwardmost position.

As an example of the tests that may be performed using the apparatus of the present invention, a test for resistance to solvents under MIL-STD-883 will be described. A plurality of packaged semiconductor devices from a particular lot or batch are divided into four equal groups, typically four packages in each group. Each group will be exposed to a particular solvent and thereafter subjected to abrasion testing by the apparatus of the present invention. Four different brushes B having predetermined bristle hardness are inserted into receptacles 56 so that a different brush can be used for each solvent. The first solvent is a mixture of isopropyl alcohol and mineral spirits (1:3,v:v) at room temperature. The semiconductor packages from the first group are immersed individually in the solvent and removed after one minutes. The devices are then placed on the support platform 12 and secured as described hereinbefore. The motor 64 is started and the first brush $B_1$ is drawn over the upper surface of the device T a total of ten times. The device T is then removed from the tester 10 and, after 5 minutes, visually inspected for any evidence of damage of degradations to the markings M (FIG. 2) on the upper surface thereof. The test is repeated for each device in the first group.

After completing the testing with the first solvent, identical tests are run with a second solvent (1,1,1-trichloroethane at room temperature), a third solvent (trichlorotrifluoroethane and methylene chloride; 50.5:49.5,w:w), and the fourth solvent (butyl Celosolve ®, monoethanolamine, and de-ionized water, 1:1:42,v:v:v). In each case, four devices shall be tested in each solvent.

Although the foregoing invention has been described in some detail by way of illustration and example for purposes of clarity of understanding, it will be obvious that certain changes and modifications may be practiced within the scope of the appended claims.

What is claimed is:

1. A reciprocating-brush testing apparatus comprising:
    a support platform;
    means mounted on the platform for removably supporting a test piece at a fixed location;
    a rod reciprocatably mounted on the platform;
    a brush holder having a predetermined weight pivotally attached at one end to the rod;
    means for reciprocating the rod to translate a brush held by the brush holder along a substantially straight path over the test piece; and
    means for periodically elevating the brush holder so that the brush will not contact the test piece during one stroke of the reciprocation cycle, but be lowered onto the test piece during the other stroke of the reciprocation cycle.

2. An apparatus as in claim 1, wherein the means for reciprocating the rod and the means for periodically elevating the brush holder are both driven by the same motor to assure that they remain in phase.

3. An apparatus as in claim 1, wherein the means for periodically elevating the brush holder is a cam which is rotated in phase with the means for reciprocating the rod.

4. A method for abrasion testing a test piece, said method employing an apparatus including:
    means for removably supporting the test piece at a fixed location;
    a brush having bristles of a predetermined hardness;
    a brush holder having a predetermined weight;
    means for horizontally reciprocating the brush holder so that the brush moves along a straight path over the semiconductor device package; and
    means for periodically elevating the brush holder in phase with the means for reciprocating the brush holder so that the brush bristles will contact the test piece with a predetermined force proportional to the weight of the brush holder during only one of the two oppositely directed strokes of the reciprocation cycle;
    said method comprising:
    placing the test piece in the support means;
    reciprocating the brush for a predetermined period of time; and
    examining the test piece for evidence of abrasion.

5. A method as in claim 4, wherein the test piece is exposed to a solvent for a predetermined period of time prior to being placed in the support means.

6. A method as in claim 5, performed in accordance with MIL-STD-883.

7. A reciprocating-brush testing apparatus comrising:
    means for removably supporting a semiconductor device package at a fixed location;
    a brush having bristles of a predetermined hardness;
    a brush holder having a predetermined weight;
    means for horizontally reciprocating the brush holder so that the brush moves along a straight path over the semiconductor device package; and
    means for periodically elevating the brush holder in phase with the means for reciprocating the brush holder so that the brush bristles will contact the semiconductor device package with a force proportional to the weight of the brush holder during only one of the two oppositely directed strokes of the horizontal reciprocation cycle.

* * * * *